United States Patent
Andaya et al.

(10) Patent No.: US 9,693,520 B1
(45) Date of Patent: Jul. 4, 2017

(54) RICE CULTIVAR M-209

(71) Applicant: CALIFORNIA COOPERATIVE RICE RESEARCH FOUNDATION, INC., Biggs, CA (US)

(72) Inventors: Virgilio Cedro Andaya, Chico, CA (US); Kent Scheidel McKenzie, Oroville, CA (US); Stanley Omar P. B. Samonte, Chico, CA (US); Farman Jodari, Chico, CA (US)

(73) Assignee: CALIFORNIA COOPERATIVE RICE RESEARCH FOUNDATION, INC., Biggs, CA (US)

( * ) Notice: Subject to any disclaimer, the term of this patent is extended or adjusted under 35 U.S.C. 154(b) by 0 days.

(21) Appl. No.: 14/983,712

(22) Filed: Dec. 30, 2015

(51) Int. Cl.
| | |
|---|---|
| A01H 5/10 | (2006.01) |
| C12N 15/82 | (2006.01) |
| A01H 1/02 | (2006.01) |
| A01H 1/06 | (2006.01) |

(52) U.S. Cl.
CPC ............. *A01H 5/10* (2013.01); *A01H 1/02* (2013.01); *A01H 1/06* (2013.01); *C12N 15/8245* (2013.01); *C12N 15/8247* (2013.01); *C12N 15/8271* (2013.01); *C12N 15/8273* (2013.01); *C12N 15/8274* (2013.01); *C12N 15/8275* (2013.01); *C12N 15/8277* (2013.01); *C12N 15/8278* (2013.01); *C12N 15/8279* (2013.01); *C12N 15/8281* (2013.01); *C12N 15/8282* (2013.01); *C12N 15/8283* (2013.01); *C12N 15/8286* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 6,492,582 B2 * | 12/2002 | Johnson | A01H 5/02 435/410 |
| 6,956,154 B2 | 10/2005 | Xie | |
| 7,301,083 B2 | 11/2007 | Sarreal et al. | |

OTHER PUBLICATIONS

Bennetzen, et al., 1992, Approaches and progress in the molecular cloning of plant disease resistance genes, *Genetic Engineering*, 14:99-124.
DeBolle, et al., 1996, Antimicrobial peptides from *Mirabilis jalapa* and *Amaranthus caudatus*: expression, processing, localization and biological activity in transgenic tobacco, *Plant Molec. Biol.*, 31:993-1008.
Eshed, et al., 1996, Less-than-additive epistatic interactions of quantitative trait loci in tomato, *Genetics*, 143:1807-1817.
Kraft, et al., 2000, Linkage disequilibrium and fingerprinting in sugar beet, *Theor. Appl. Genet.*, 101:323-326.
McKenzie, et al., 1994, Breeding improved rice cultivars for temperate regions: a case study, *Australian Journal of Experimental Agriculture*, 34:897-905.
Pang, et al., 1992, Expression of a gene encoding a scorpion insectotoxin peptide in yeast, bacteria and plants, *Gene*, 116:165-172.
Poehlman, J.M. and Sleper, D.A., Breeding Field Crops, 4th Ed. 1995, Iowa State University Press, p. 473.
Smith, C.W. and Dilday, R.H., Origin, Domestication, and Diversification in Rice: Origin, History, Technology, and Production, 2003, John Wiley & Sons, Inc., pp. 4-6.
Yu, et al., 1997, Importance of epistasis as the genetic basis of heterosis in an elite rice hybrid, *Proc. Natl. Acad. Sci.*, 94:9226-9231.

* cited by examiner

*Primary Examiner* — Medina A Ibrahim
(74) *Attorney, Agent, or Firm* — Jondle & Associates, P.C.

(57) ABSTRACT

A rice cultivar designated M-209 is disclosed. The invention relates to the seeds of rice cultivar M-209, to the plants of rice M-209 and to methods for producing a rice plant produced by crossing the cultivar M-209 with itself or another rice variety. The invention further relates to hybrid rice seeds and plants produced by crossing the cultivar M-209 with another rice cultivar.

29 Claims, No Drawings

RICE CULTIVAR M-209

BACKGROUND OF THE INVENTION

The present invention relates to a new and distinctive rice cultivar designated M-209. All publications cited in this application are herein incorporated by reference.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. For the dry-seeded system, when the plants have reached sufficient size (four- to five-leaf stage), a shallow permanent flood of water 5 to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium grain and short-grain. Typical U.S. long-grain cultivars cook dry and fluffy when steamed or boiled, whereas medium- and short-grain cultivars cook moist and sticky. Long-grain cultivars have been traditionally grown in the southern states and generally receive higher market prices.

Rice, *Oryza sativa* L., is an important and valuable field crop. Thus, a continuing goal of plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there is provided a novel rice cultivar designated M-209. This invention thus relates to the seeds of rice cultivar M-209, to the plants of rice M-209 and to methods for producing a rice plant produced by crossing the rice M-209 with itself or another rice line.

Thus, any such methods using the rice variety M-209 are part of this invention: selfing, backcrosses, hybrid production, crosses to populations, and the like. All plants produced using rice variety M-209 as a parent are within the scope of this invention. Advantageously, the rice variety could be used in crosses with other, different, rice plants to produce first generation ($F_1$) rice hybrid seeds and plants with superior characteristics.

In another aspect, the present invention provides for single gene converted plants of M-209. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant M-209. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, leaves, anthers, root tips, flowers, seeds, panicles or stems. Still further, the present invention provides rice plants regenerated from the tissue cultures of the invention.

In addition to the exemplary aspects and embodiments described above, further aspects and embodiments will become apparent by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Aggregate sheath spot. Is caused by the fungus *Rhizoctonia oryzae-sativae* (Sawada) Mordue (=*Ceratobasidium oryzae-sativae*). This disease causes sheath lesions and can reduce yield and grain quality. California varieties generally rate between 2 and 4 in greenhouse tests on a scale of 0 to 4.

Alkali spreading value. Indicator of gelatinization temperature and an index that measures the extent of disintegration of milled rice kernel in contact with dilute alkali solution. Standard long grains have 3 to 5 Alkali Spreading Value (intermediate gelatinization temperature). Standard medium and short grain rice have 6 to 7 Alkali Spreading Values (low gelatinization temperature).

Allele. Allele is any of one or more alternative forms of a gene, all of which alleles relate to one trait or characteristic. In a diploid cell or organism, the two alleles of a given gene occupy corresponding loci on a pair of homologous chromosomes.

Alter. The utilization of up-regulation, down-regulation, or gene silencing.

Apparent amylose percent. The most important grain characteristic that describes cooking behavior in each grain class, or type, i.e., long, medium and short grain. The percentage of the endosperm starch of milled rice that is amylose. Standard long grains contain 20 to 23% amylose. Rexmont type long grains contain 24 to 25% amylose. Short and medium grain rice contain 16 to 19% amylose. Waxy rice contains 0% amylose. Amylose values will vary over environments.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bakanae. Is caused by the fungus *Fusarium fujikuroi* Nirenberg (=*Gibberella fujikuroi*). It causes reduced seed germination and abnormal seedling elongation often followed by crown rot. Susceptibility of varieties is expressed as percent symptomatic plants.

Blanking %. Visual estimate of the percent of sterile florets (florets that are empty with no filled kernels) in the panicle as a measurement of cool temperature induced pollen sterility. Blanking may also be induced by high temperatures and by genetic incompatibility of the parents. This data may be collected in screening nurseries at cool locations, cool years, and also in screening tests in refrigerated greenhouses.

Breakdown. The peak viscosity minus the hot paste viscosity.

Breeding. The genetic manipulation of living organisms.

Cell. Cell as used herein includes a plant cell, whether isolated, in tissue culture or incorporated in a plant or plant part.

Cross-pollination. Fertilization by the union of two gametes from different plants.

Cool paste viscosity. Viscosity measure of rice flour/water slurry after being heated to 95EC and uniformly cooled to 50EC (American Association of Cereal Chemist). Values less than 200 for cool paste indicate softer cooking types of rice.

Days to 50% heading. Average number of days from planting to the day when 50% of all panicles are exerted at least partially through the leaf sheath. A measure of maturity.

Diploid. A cell or organism having two sets of chromosomes.

Elongation. Cooked kernel elongation is the ratio of the cooked kernel length divided by the uncooked kernel length. Extreme cooked kernel elongation is a unique feature of basmati type rice and an important quality criterion for that market type.

Embryo. The embryo is the small plant contained within a mature seed.

Essentially all the physiological and morphological characteristics. A plant having essentially all the physiological and morphological characteristics means a plant having the physiological and morphological characteristics of the cultivar, except for the characteristics derived from the converted gene.

$F_\#$. The "F" symbol denotes the filial generation, and the # is the generation number, such as $F_1$, $F_2$, $F_3$, etc.

Final viscosity. Viscosity at the end of the test or cold paste.

Gene. As used herein, "gene" refers to a unit of inheritance corresponding to DNA or RNA that code for a type of protein or for an RNA chain that has a function in the organism.

Gene silencing. The interruption or suppression of the expression of a gene at the level of transcription or translation.

Genotype. Refers to the genetic constitution of a cell or organism.

Grain length (L). Length of a rice grain is measured in millimeters.

Grain width (W). Width of a rice grain is measured in millimeters.

Grain yield. Grain yield is measured in pounds per acre and at 14.0% moisture. Grain yield of rice is determined by the number of panicles per unit area, the number of fertile florets per panicle, and grain weight per floret.

Haploid. A cell or organism having one set of the two sets of chromosomes in a diploid.

Harvest moisture. The percent of moisture of the grain when harvested.

Head rice. Unbroken kernels of milled rice.

Hot paste viscosity. Viscosity measure of rice flour/water slurry after being heated to 95EC. Lower values indicate softer and stickier cooking types of rice.

Length/Width (L/W) ratio. This ratio is determined by dividing the average length (L) by the average width (W).

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A defined segment of DNA.

Lodging resistance (also called Straw strength). Lodging is measured as a subjective rating and is percentage of the plant stems leaning or fallen completely to the ground before harvest. Visual scoring where 0%=all plants standing to 100%=all plant in plot are laying flat on the soil surface. Lodged plants are difficult to harvest and reduce yield and grain quality.

Milling yield. Milling yield is the total amount of milled rice (whole and broken kernels) recovered after removal of hulls, bran, and germ by milling and head-rice yield, the total amount of whole kernels recovered after milling. Values are expressed as weight percentage of the original paddy or rough rice sample that was milled. For example, a milling yield of 65/70 is a sample of 100 grams of rough rice that produced 65 grams of head rice and 70 grams of total milled rice.

Nucleic acid. An acidic, chainlike biological macromolecule consisting of multiple repeat units of phosphoric acid, sugar and purine and pyrimidine bases.

Nutraceutical. Refers to a food or food product that provides health and or medical benefits, including the prevention and treatment of disease. Such products may range from isolated nutrients, dietary supplements and specific diets to genetically engineered foods, herbal products, and processed foods such as cereals, soups and beverages.

1000 Grain wt. The weight of 1000 rice grains as measured in grams. It can be for paddy, brown or milled rice.

Pedigree. Refers to the lineage or genealogical descent of a plant.

Pedigree distance. Relationship among generations based on their ancestral links as evidenced in pedigrees. May be measured by the distance of the pedigree from a given starting point in the ancestry.

Percent identity. Percent identity as used herein refers to the comparison of the homozygous alleles of two rice varieties. Percent identity is determined by comparing a statistically significant number of the homozygous alleles of two developed varieties. For example, a percent identity of 90% between rice variety 1 and rice variety 2 means that the two varieties have the same allele at 90% of their loci.

Peak viscosity. The maximum viscosity attained during heating when a standardized instrument-specific protocol is applied to a defined rice flour-water slurry.

Plant. As used herein, the term "plant" includes reference to an immature or mature whole plant, including a plant from which seed, grain, or anthers have been removed. Seed or embryo that will produce the plant is also considered to be the plant.

Plant height. Plant height measured in centimeters or inches is taken from soil surface to the tip of the extended panicle at harvest.

Plant parts. As used herein, the term "plant parts" (or a rice plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Progeny. As used herein, includes an $F_1$ rice plant produced from the cross of two rice plants where at least one plant includes rice cultivar M-209 and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Quantitative Trait Loci (QTL). Quantitative trait loci (QTL) refer to genetic loci that control to some degree numerically representable traits that are usually continuously distributed.

RVA viscosity. Rapid Visco Analyzer is a widely used laboratory instrument to examine paste viscosity, or thickening ability of milled rice during the cooking process.

RVU. The RVA scale is measured in RVUs. This is the native viscosity unit of the RVA. 1 RVU is equivalent to 12 CP. CP equals "centipoises" which equals unit of viscosity (kg s$^{-1}$ m$^{-1}$) and 1 kg s$^{-1}$ m$^{-1}$ equals 1000 centipoises.

Regeneration. Regeneration refers to the development of a plant from tissue culture.

Setback. Setback 1 is the final viscosity minus trough viscosity. Setback 2 is the final viscosity minus peak viscosity and is what is most commonly referred to for rice quality testing.

Single gene converted (Conversion). Single gene converted (conversion), also known as coisogenic plants, refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stem rot. Is caused by the fungus *Sclerotium oryzae* Cattaneo (=*Magnaporthe salvinii*). It produces sheath and stem lesions that can reduce yield and grain quality. California varieties are generally rated between 4.5 and 7.5 on a scale of 0 to 10.

Texture score. A relative subjective score used by the breeder in evaluating cooked rice samples. A score of 4 being most sticky and a score of 2 being the least sticky.

Trough viscosity. The minimum viscosity after the peak, normally occurring when the sample starts to cool.

Rice cultivar M-209 is a semi-dwarf, early maturing, glabrous, Calrose-type medium grain rice. It was derived from a cross made at the Rice Experiment Station (RES) in 2004 designated R29174 with the pedigree M-205/5/M-201/M7//M-201/3/M-202/4/M-204. The detailed pedigree information is as follows: R29174=M-205/03-Y-605; where 03-Y-605=90-Y-63/M-202//M-204, and 90-Y-63=M-201/M7//M-201. M-205 (U.S. PVP 200100058; U.S. Pat. No. 6,492,582) is a high yielding, glabrous, early maturing Calrose variety released by RES in 2005 and adapted in warmer and more favorable rice growing areas in California. M-202 is a popular photoperiod insensitive, early maturing, cold tolerant, semi-dwarf medium grain released by RES in 1985. M-201 released in 1982, has short stature and early maturity while M7 is a late maturing, glabrous, short statured medium grain released in 1977. M-204 (U.S. PVP 9300075) was released in 1992 and is photoperiod insensitive, early maturing, glabrous, semi dwarf medium grain variety. M7, M-201 and M-204 are no longer in commercial production in California.

Rice cultivar M-209 was developed using the pedigree selection method and underwent 12 years (14 generations) of selection and evaluation from the original cross until the production of its foundation seed. It was tested under the experimental designation of 08Y3269 in the University of California Cooperative Extension (UCCE) Statewide (SW) Yield Tests from 2010-2014 in a total of 38 experiments. Rice cultivar M-209 (08Y3269) was also evaluated in three strip trial sites (Colusa, Butte, Glenn counties) in 2013.

Rice cultivar M-209 is California Calrose medium grain rice that can be classified as Gramineae, *Oryza sativa* L., and temperate *japonica*. Rice cultivar M-209 is a photoperiod insensitive, early maturing semidwarf cultivar having awnless lemma and palea and glabrous hulls and leaves. Rice cultivar M-209 is most similar to rice cultivar M-205 (U.S. PVP 200100058; U.S. Pat. No. 6,492,582) and is distinguished by having a larger kernel size, earlier days to heading and higher yield potential. M-209 heads later than M-206 (U.S. PVP 200100180; U.S. Pat. No. 6,911,589) and M-202, and has shown a higher yield potential.

Rice cultivar M-209 has shown yield advantages of about 10%, 6%, and 2% over M-202, M-205, and M-206, respectively, using the overall average of 5-year multi-location experiments in UCCE Statewide Tests. Compared to M-205, rice cultivar M-209 heads two days earlier, has slightly larger grains, and wider area of adaptation. Rice cultivar M-209 is intended in areas where M-205 and M-202 are grown and is competitive in areas where M-206 is grown, especially in more favorable rice growing environments.

Rice cultivar M-209 has shown uniformity and stability as described in the following variety description information. It has been self-pollinated a sufficient number of generations with careful attention to uniformity of plant type. The line has been increased with continued observation for uniformity.

Rice cultivar M-209 has the following morphologic and other characteristics (based primarily on data collected in California).

TABLE 1

VARIETY DESCRIPTION INFORMATION

Grain type: Medium
Days to maturity (50% heading): 87
Culm:

Angle (degrees from perpendicular after flowering): Erect (less than 30°)
Length (soil level to top of extended panicle on main stem): 98.1 cm
Height class: Short
Internode color (after flowering): Green
Strength (lodging resistance): Strong (no lodging)
Flag leaf (at maturity):

Length: 37.2 cm
Width: 14.5 mm
Pubescence: Glabrous
Leaf angle (after heading): Erect
Blade color (at heading): Green
Basal leaf sheath color (at heading): Green
Ligule:

Length (from base of collar to the tip, at late vegetative stage): 16.5 mm
Color (late vegetative stage): White
Shape: Acute to Acuminate
Collar Color (late vegetative stage): Pale green
Auricle Color (late vegetative stage): Pale green
Panicle:

Length: 19.8 cm
Type: Intermediate
Secondary branching: Light
Exertion (near maturity): 100% Exerted
Shattering (at maturity): Low (less than 5%)
Threshability: Easy
Grain (spikelet):

Awns (after full heading): Short and partly awned
Apiculus color (at maturity): Straw
Apiculus color (after full heading): Straw
Stigma color: White
Lemma and palea color (at maturity): Straw
Lemma and palea pubescence: Hairs on lemma keel
Spikelet sterility (at maturity): Highly fertile (>90%)
Grain (seed):

Seed coat color: Light brown
Endosperm type: Nonglutinous (nonwaxy)
Endosperm translucency: Clear
Endosperm chalkiness: None
Scent: Nonscented
Shape class (length/width ratio):
Paddy:    Medium (2.3:1 to 3.3:1)
              Length: 8.47 mm
              Width: 3.2 mm
              L/W ratio: 2.64
              1000 Grains: 29.7 g
Brown:    Medium (2.1:1 to 3.3:1)
              Length: 6.23 mm
              Width: 2.78 mm
              L/W ratio: 2.24
              1000 Grains: 24.6 g
Milled:    Medium (2.0:1 to 3.3:1)
              Length: 5.94 mm
              Width: 2.7 mm
              L/W ratio: 2.2
              1000 Grains: 22.1 g TABLE 1-continued

VARIETY DESCRIPTION INFORMATION

Milling quality (% hulls): 20.0
Milling yield (% whole kernel (head) rice to rough rice): 65/71
% Protein (brown): 6.3
% Amylose: 17.1
Alkali spreading value:

Gelatinization temperature type: Low amylographic paste viscosity
Amylographic paste viscosity (RVA measured in RVU):
Peak: 234.6
Hot paste: 123.0
Cooled paste: 233.2
Setback: −1.4
Resistance to low temperature:

Germination and seedling vigor: High
Flowering (spikelet fertility): High
Seedling vigor not related to low temperature: High
Disease resistance:

Rice blast (*Pyricularia oryzae*): Susceptible to races in California
Aggregate sheath spot (*Rhizoctonia oryzae-sativae*): Moderately susceptible
Stem rot (*Sclerotium oryzae*): Intermediate
Insect resistance: None This invention also is directed to methods for producing a rice plant by crossing a first parent rice plant with a second parent rice plant wherein either the first or second parent rice plant is a rice plant of the line M-209. Further, both first and second parent rice plants can come from the rice cultivar M-209. Still further, this invention also is directed to methods for producing a rice cultivar M-209-derived rice plant by crossing rice cultivar M-209 with a second rice plant and growing the progeny seed, and repeating the crossing and growing steps with the rice cultivar M-209-derived plant from 0 to 7 times. Thus, any such methods using the rice cultivar M-209 are part of this invention: selfing, backcrosses, hybrid production, crosses to populations, and the like. All plants produced using rice cultivar M-209 as a parent are within the scope of this invention, including plants derived from rice cultivar M-209. Advantageously, the rice cultivar is used in crosses with other, different, rice cultivars to produce first generation ($F_1$) rice seeds and plants with superior characteristics.

It should be understood that the cultivar can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like.

Further Embodiments of the Invention

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years, several methods for producing transgenic plants have been developed, and the present invention, in particular embodiments, also relates to transformed versions of the claimed cultivar.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation", in *Methods in Plant Molecular Biology & Biotechnology* in Glich, et al., (Eds. pp. 89-119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include the direct infection or co-cultivation of plant cells with *Agrobacterium tumefaciens*, described for example by Horsch et al., *Science*, 227:1229 (1985). Descriptions of *Agrobacterium* vector systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using a microprojectile media delivery system with a biolistic device or using *Agrobacterium*-mediated transformation. Transformant plants obtained with the protoplasm of the invention are intended to be within the scope of this invention.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO96/30530.

C. Tissue-specific or Tissue-preferred Promoters—A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is rice. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defences are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content, 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene; 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271-282 (1994) and U.S. Pat.

No. 5,591,616 issued Jan. 7, 1997. Several methods of plant transformation collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Additionally, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of rice target tissues, expression of the above-described selectable marker genes allows for preferential selection of transformed cells, tissues and/or plants, using regeneration and selection methods now well known in the art.

The foregoing methods for transformation would typically be used for producing a transgenic cultivar. The transgenic cultivar could then be crossed, with another (non-transformed or transformed) cultivar, in order to produce a new transgenic cultivar. Alternatively, a genetic trait which has been engineered into a particular rice cultivar using the foregoing transformation techniques could be moved into another cultivar using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar which does not contain that gene. As used herein, "crossing" can refer to a simple X by Y cross, or the process of backcrossing, depending on the context.

Single Gene Conversion

When the term rice plant is used in the context of the present invention, this also includes any single gene conversions of that cultivar. The term single gene converted plant as used herein refers to those rice plants which are developed by a plant breeding technique called backcrossing wherein essentially all of the desired morphological and physiological characteristics of a cultivar are recovered in addition to the single gene transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental rice plants, the recurrent parent, for that cultivar, i.e., backcrossing 1, 2, 3, 4, 5, 6, 7, 8, 9 or more times to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent as determined at the 5% significance level when grown in the same environmental conditions.

The selection of a suitable recurrent parent is an important step for a successful backcrossing procedure. The goal of a backcross protocol is to alter or substitute a single trait or characteristic in the original cultivar. To accomplish this, a single gene of the recurrent cultivar is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of rice and regeneration of plants therefrom is well known and widely published. For example, reference may be had to Komatsuda, T. et al., *Crop Sci.* 31:333-337 (1991); Stephens, P. A., et al., *Theor. Appl. Genet.* (1991) 82:633-635; Komatsuda, T. et al., *Plant Cell, Tissue and Organ Culture*, 28:103-113 (1992); Dhir, S. et al., *Plant Cell Reports* (1992)

11:285-289; Pandey, P. et al., *Japan J Breed.* 42:1-5 (1992); and Shetty, K., et al., *Plant Science* 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce rice plants having the physiological and morphological characteristics of rice variety M-209.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, pistils, anthers and the like. Thus, another aspect of this invention is to provide for cells which upon growth and differentiation produce a cultivar having essentially all of the physiological and morphological characteristics of M-209.

The present invention contemplates a rice plant regenerated from a tissue culture of a variety (e.g., M-209) or hybrid plant of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., (1999) "Use of bridging parents with high anther culturability to improve plant regeneration and breeding value in rice", *Rice Biotechnology Quarterly* 38:25-26; Chu, Q. R., et al., (1998), "A novel plant regeneration medium for rice anther culture of Southern U.S. crosses", *Rice Biotechnology Quarterly* 35:15-16; Chu, Q. R., et al., (1997), "A novel basal medium for embryogenic callus induction of Southern US crosses", *Rice Biotechnology Quarterly* 32:19-20; and Oono, K., "Broadening the Genetic Variability By Tissue Culture Methods", *Jap. J. Breed.* 33 (Suppl.2), 306-307, illus. 1983. Thus, another aspect of this invention is to provide cells which upon growth and differentiation produce rice plants having the physiological and morphological characteristics of variety M-209.

Duncan, et al., *Planta* 165:322-332 (1985) reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports* 7:262-265 (1988), reports several media additions that enhance regenerability of callus of two cultivars. Other published reports also indicated that "non-traditional" tissues are capable of producing somatic embryogenesis and plant regeneration. K. P. Rao et al., *Maize Genetics Cooperation Newsletter,* 60:64-65 (1986), refers to somatic embryogenesis from glume callus cultures and B. V. Conger, et al., *Plant Cell Reports,* 6:345-347 (1987) indicates somatic embryogenesis from the tissue cultures of corn leaf segments. Thus, it is clear from the literature that the state of the art is such that these methods of obtaining plants are routinely used and have a very high rate of success. Thus, another aspect of this invention is to provide cells which upon growth and differentiation produce rice plants having the physiological and morphological characteristics of rice cultivar M-209.

The utility of rice cultivar M-209 also extends to crosses with other species. Commonly, suitable species will be of the family Graminaceae, and especially of the genera *Zea, Tripsacum, Croix, Schlerachne, Polytoca, Chionachne,* and *Trilobachne,* of the tribe Maydeae.

Additional Breeding Methods

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better grain quality including improve physical appearance, cooking and taste characteristics, and milling yield (% whole kernel milled rice or head rice and % total milled rice).

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of rice plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior hybrid crosses. The hybrid seed is produced by manual crosses between selected male-fertile parents or by using male sterility systems. These hybrids are selected for certain single gene traits such as semi-dwarf plant type, pubescence, awns, and apiculus color which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin with evaluation of $F_1$ plants, continue with selection of $F_2$ plants, and on in the $F_3$, where the best individuals in the best families are selected and advanced. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987; Marshall and Wadsworth, 1994; Champagne, 2004).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

This invention also is directed to methods for producing a rice plant by crossing a first parent rice plant with a second parent rice plant wherein the first or second parent rice plant is a rice plant of the variety M-209. Further, both first and second parent rice plants can come from the rice variety M-209. Thus, any such methods using the rice variety M-209 are part of this invention: selfing, backcrosses, hybrid production, crosses to populations, and the like. All plants produced using rice variety M-209 as a parent are within the scope of this invention, including those developed from varieties derived from rice variety M-209. Advantageously, the rice variety could be used in crosses with other, different, rice plants to produce the first generation ($F_1$) rice hybrid seeds and plants with superior characteristics. The variety of the invention can also be used for transformation where exogenous genes are introduced and expressed by the variety of the invention. Genetic variants created either through traditional breeding methods using variety M-209 or through transformation of M-209 by any of a number of protocols known to those of skill in the art are intended to be within the scope of this invention.

The following describes breeding methods that may be used with cultivar M-209 in the development of further rice plants. One such embodiment is a method for developing an M-209 progeny rice plant in a rice plant breeding program comprising: obtaining the rice plant, or a part thereof, of cultivar M-209 utilizing said plant or plant part as a source of breeding material and selecting an M-209 progeny plant with molecular markers in common with M-209 and/or with morphological and/or physiological characteristics selected from the characteristics listed in Tables 1-7. Breeding steps that may be used in the rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar M-209 progeny rice plants, comprising crossing cultivar M-209 with another rice plant, thereby producing a population of rice plants, which, on average, derive 50% of their alleles from cultivar M-209. A plant of this population may be selected and repeatedly selfed or sibbed with a rice cultivar resulting from these successive filial generations. One embodiment of this invention is the rice cultivar produced by this method and that has obtained at least 50% of its alleles from cultivar M-209.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes rice cultivar M-209 progeny rice plants comprising a combination of at least two M-209 traits selected from the group consisting of those listed in Tables 1-10 or the M-209 combination of traits listed in the Summary of the Invention, so that said progeny rice plant is not significantly different for said traits than rice cultivar M-209 as determined at the 5% significance level when grown in the same environment. Using techniques described herein, molecular markers may be used to identify said progeny plant as a M-209 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar M-209 may also be characterized through their filial relationship with rice cultivar M-209, as for example, being within a certain number of breeding crosses of rice cultivar M-209. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice cultivar M-209 and its progeny. For example, progeny produced by the methods described herein may be within 1, 2, 3, 4, 5, 6 or 7 breeding crosses of rice cultivar M-209.

The seed of rice cultivar M-209, the plant produced from the cultivar seed, the hybrid rice plant produced from the crossing of the cultivar, hybrid seed, and various parts of the hybrid rice plant and transgenic versions of the foregoing, can be utilized for human food, livestock feed, and as a raw material in industry.

Tables

Table 2 shows the results of the University of California Cooperative Extension Statewide Yield Tests for the Early group from 2010 to 2014 for rice cultivar M-209 (experimental designation 08Y3269) compared to current medium grain varieties M-202, M-205, and M-206. The test plots were 10×20 foot plots and tests were performed in four replications in commercial growers' fields and Rice Experiment Station (RES) in Biggs, Calif., Butte County, Colusa County, and Yuba County. Values are averages of entries from tests. Column 1 shows the location and entry, columns 2-11 show the grain yield (lb/a) and significance for 2010, 2011, 2012, 2013 and 2014, and columns 12-21 show the days to 50% heading and significance for 2010, 2011, 2012, 2013 and 2014. In Table 2, "ns" indicates that the entry is not significantly different from M-209 at p=0.05, while "*" indicates that the entry is significantly different from M-209 at p=0.05.

TABLE 2

| Location Entry | Grain Yield (lb/a) | | | | | | | | | | Days to 50% Heading | | | | | | | | | |
|---|---|---|---|---|---|---|---|---|---|---|---|---|---|---|---|---|---|---|---|---|
| | 2010 | | 2011 | | 2012 | | 2013 | | 2014 | | 2010 | | 2011 | | 2012 | | 2013 | | 2014 | |
| RES | | | | | | | | | | | | | | | | | | | | |
| M-209 | 10930 | — | 10867 | — | 9870 | — | 9070 | — | 9670 | — | 90 | — | 93 | — | 87 | — | 87 | — | 87 | — |
| M-202 | 10210 | ns | 9660 | * | 9770 | ns | 7640 | * | 7010 | * | 91 | ns | 90 | * | 87 | ns | 85 | * | 88 | ns |
| M-205 | 10790 | ns | 10610 | ns | 10530 | ns | 9230 | ns | 9140 | ns | 92 | * | 93 | ns | 88 | ns | 88 | ns | 89 | ns |
| M-206 | 10990 | ns | 10047 | * | 9980 | ns | 8160 | * | 9240 | ns | 84 | * | 88 | * | 84 | * | 82 | * | 80 | * |
| CV (%) | 6 | | 3 | | 8 | | 7 | | 5 | | 1 | | 1 | | 1 | | 1 | | 2 | |
| LSD (.05) | 870 | | 490 | | 1070 | | 870 | | 540 | | 1 | | 2 | | 1 | | 1 | | 2 | |
| Butte | | | | | | | | | | | | | | | | | | | | |
| M-209 | 9380 | — | 9520 | — | 10210 | — | 8570 | — | 9140 | — | 87 | — | 96 | — | 85 | — | 88 | — | 84 | — |
| M-202 | 8190 | * | 8180 | * | 8650 | * | 7870 | * | 8360 | * | 84 | * | 91 | * | 84 | ns | 89 | ns | 87 | * |
| M-205 | 7950 | * | 8860 | ns | 9600 | * | 8960 | * | 9140 | ns | 87 | ns | 96 | ns | 87 | * | 91 | * | 87 | * |
| M-206 | 8440 | * | 8520 | * | 9240 | * | 9020 | * | 9610 | * | 81 | * | 89 | * | 80 | * | 83 | * | 79 | * |
| CV (%) | 5 | | 7 | | 4 | | 3 | | 3 | | 1 | | 1 | | 1 | | 2 | | 1 | |
| LSD (.05) | 610 | | 830 | | 500 | | 400 | | 400 | | 2 | | 1 | | 1 | | 2 | | 1 | |
| Colusa | | | | | | | | | | | | | | | | | | | | |
| M-209 | 11110 | — | 10210 | — | 10100 | — | 9730 | — | 9600 | — | 98 | — | 96 | — | 92 | — | 90 | — | 90 | — |
| M-202 | 10910 | ns | 9350 | ns | 8630 | * | 9140 | ns | 8720 | * | 94 | * | 91 | * | 87 | * | 90 | ns | 86 | * |
| M-205 | 11190 | ns | 9760 | ns | 9130 | * | 8930 | ns | 9370 | ns | 99 | ns | 101 | * | 94 | ns | 93 | * | 90 | ns |
| M-206 | 10560 | ns | 9960 | ns | 9680 | ns | 9660 | ns | 9280 | ns | 91 | * | 89 | * | 86 | * | 86 | * | 83 | * |
| CV (%) | 5 | | 9 | | 5 | | 7 | | 6 | | 1 | | 3 | | 2 | | 2 | | 1 | |
| LSD (.05) | 800 | | 1200 | | 660 | | 890 | | 730 | | 2 | | 3 | | 2 | | 2 | | 1 | |
| Yuba | | | | | | | | | | | | | | | | | | | | |
| M-209 | 10320 | — | 10260 | — | 9010 | — | 9690 | — | 8800 | — | 93 | — | 101 | — | 96 | — | 91 | — | 92 | — |
| M-202 | 10220 | ns | 9300 | * | 9220 | ns | 8950 | * | 8010 | ns | 91 | ns | 97 | * | 89 | * | 92 | ns | 90 | ns |
| M-205 | 9370 | * | 10000 | ns | 8840 | ns | 9650 | ns | 9120 | ns | 94 | ns | 102 | ns | 94 | * | 96 | * | 93 | ns |
| M-206 | 10330 | ns | 10190 | ns | 9240 | ns | 9750 | ns | 8950 | ns | 85 | * | 94 | * | 87 | * | 87 | * | 84 | * |
| CV (%) | 5 | | 6 | | 5 | | 3 | | 6 | | 1 | | 1 | | 1 | | 1 | | 2 | |
| LSD (.05) | 610 | | 820 | | 550 | | 450 | | 790 | | 2 | | 1 | | 1 | | 1 | | 3 | |

Table 3 shows the results of the University of California Cooperative Extension Statewide Yield Tests for the Very Early group from 2010 to 2014 for rice cultivar M-209 (experimental designation 08Y3269) compared to current medium grain varieties M-202, M-205, and M-206. The test plots were 10×20 foot plots and tests were performed in four replications in commercial growers' fields and Rice Experiment Station (RES) in Biggs, Calif., San Joaquin County, Yolo County, and Sutter County. Values are averages of entries from tests. Column 1 shows the location and entry, columns 2-7 show the grain yield (lb/a) and significance for 2012, 2013 and 2014, and columns 8-13 show the days to 50% heading and significance for 2012, 2013 and 2014. In Table 3, "ns" indicates that the entry is not significantly different from M-209 at p=0.05, while "*" indicates that the entry is significantly different from M-209 at p=0.05.

TABLE 3

| Location Entry | Grain Yield (lb/a) | | | | | | Days to 50% Heading | | | | | |
|---|---|---|---|---|---|---|---|---|---|---|---|---|
| | 2012 | | 2013 | | 2014 | | 2012 | | 2013 | | 2014 | |
| RES | | | | | | | | | | | | |
| M-209 | 10360 | — | 10860 | — | 10070 | — | 86 | — | 91 | — | 84 | — |
| M-202 | 10050 | ns | 8380 | * | 7330 | * | 89 | * | 89 | ns | 84 | ns |
| M-205 | 10220 | ns | 9030 | * | 9770 | ns | 88 | ns | 92 | ns | 86 | * |
| M-206 | 10420 | ns | 8610 | * | 9200 | * | 84 | ns | 82 | * | 79 | * |
| CV (%) | 6 | | 6 | | 5 | | 2 | | 2 | | 1 | |
| LSD (.05) | 860 | | 780 | | 600 | | 2 | | 2 | | 1 | |
| San Joaquin | | | | | | | | | | | | |
| M-209 | 6910 | — | 8580 | — | 9350 | — | 118 | — | 113 | — | 101 | — |
| M-202 | 7490 | * | 8140 | ns | 8650 | * | 115 | * | 109 | * | 102 | ns |
| M-205 | 4570 | * | 7740 | * | 8810 | * | 126 | * | 114 | ns | 104 | * |
| M-206 | 8990 | * | 8410 | ns | 9390 | ns | 106 | * | 100 | * | 94 | * |
| CV (%) | 4 | | 4 | | 4 | | 1 | | 1 | | 1 | |
| LSD (.05) | 470 | | 480 | | 450 | | 1 | | 1 | | 1 | |
| Yolo | | | | | | | | | | | | |
| M-209 | 9720 | — | 9390 | — | 9960 | — | 92 | — | 85 | — | 93 | — |
| M-202 | 8930 | * | 9260 | ns | 9450 | ns | 90 | * | 84 | ns | 93 | ns |
| M-205 | 9310 | ns | 9580 | ns | 9780 | ns | 93 | ns | 87 | * | 95 | * |
| M-206 | 9900 | ns | 9790 | * | 9770 | ns | 91 | ns | 80 | * | 85 | * |
| CV (%) | 5 | | 3 | | 7 | | 1 | | 1 | | 1 | |
| LSD (.05) | 600 | | 380 | | 910 | | 1 | | 1 | | 1 | |

TABLE 3-continued

| Location | Grain Yield (lb/a) | | | | | | Days to 50% Heading | | | | | |
|---|---|---|---|---|---|---|---|---|---|---|---|---|
| Entry | 2012 | | 2013 | | 2014 | | 2012 | | 2013 | | 2014 | |
| Sutter | | | | | | | | | | | | |
| M-209 | 9190 | — | 10320 | — | 9310 | — | 88 | — | 92 | — | 88 | — |
| M-202 | 8810 | ns | 9990 | ns | 9060 | ns | 87 | ns | 92 | ns | 92 | * |
| M-205 | 8940 | ns | 9850 | * | 9170 | ns | 90 | * | 92 | ns | 91 | * |
| M-206 | 9320 | ns | 9710 | * | 9710 | ns | 86 | * | 85 | * | 80 | * |
| CV (%) | 3 | | 3 | | 5 | | 1 | | 1 | | 1 | |
| LSD (.05) | 410 | | 420 | | 670 | | 1 | | 1 | | 1 | |

Table 4 shows the results of the University of California Cooperative Extension Statewide Yield Tests for the Intermediate-Late group from 2013 to 2014 for rice cultivar M-209 (experimental designation 08Y3269) compared to current medium grain varieties M-202, M-205, and M-206. The test plots were 10×20 foot plots and tests were performed in four replications in commercial growers' fields and Rice Experiment Station (RES) in Biggs, Calif., Glenn County, and Sutter County. Values are averages of entries from tests. Column 1 shows the location and entry, columns 2-5 show the grain yield (lb/a) and significance for 2013 and 2014, and columns 6-9 show the days to 50% heading and significance for 2013 and 2014. In Table 4, "ns" indicates that the entry is not significantly different from M-209 at p=0.05, while "*" indicates that the entry is significantly different from M-209 at p=0.05.

TABLE 4

| Location | Grain Yield (lb/a) | | | | Days to 50% Heading | | | |
|---|---|---|---|---|---|---|---|---|
| Entry | 2013 | | 2014 | | 2013 | | 2014 | |
| RES | | | | | | | | |
| M-209 | 10100 | — | 11270 | — | 86 | — | 86 | — |
| M-202 | 8700 | * | 8870 | * | 85 | ns | 85 | ns |
| M-205 | 9730 | ns | 10550 | ns | 88 | ns | 87 | ns |
| M-206 | 9570 | ns | 10570 | ns | 81 | * | 79 | * |
| CV (%) | 5 | | 5 | | 2 | | 2 | |
| LSD (.05) | 620 | | 720 | | 2 | | 2 | |
| Glenn | | | | | | | | |
| M-209 | 8490 | — | 8610 | — | 97 | — | 91 | — |
| M-202 | 8270 | ns | 8510 | ns | 97 | ns | 89 | * |
| M-205 | 8400 | ns | 8910 | ns | 99 | ns | 93 | * |
| M-206 | 9390 | * | 8270 | ns | 86 | * | 87 | * |
| CV (%) | 4 | | 5 | | 2 | | 1 | |
| LSD (.05) | 470 | | 630 | | 2 | | 1 | |
| Sutter | | | | | | | | |
| M-209 | 8150 | — | 10010 | — | 91 | — | 89 | — |
| M-202 | 7890 | ns | 9030 | ns | 89 | * | 88 | ns |
| M-205 | 8540 | ns | 8680 | ns | 93 | * | 91 | * |
| M-206 | 8820 | ns | 9270 | ns | 86 | * | 82 | * |
| CV (%) | 7 | | 11 | | 1 | | 1 | |
| LSD (.05) | 850 | | 1350 | | 1 | | 1 | |

Table 5 shows the average values for agronomic characteristics for rice cultivar M-209 (experimental designation 08Y3269) from the University of California Cooperative Extension Statewide Yield Tests for the Very Early, Early and Intermediate-Late groups from 2010 to 2014. The test plots were 10×20 foot plots and tests were performed in four replications in commercial growers' fields and Rice Experiment Station (RES) in Biggs, Calif., Glenn County, Butte, Yolo County, Yuba County and Sutter County. Values are averages of entries from all test years and locations. Column 1 shows the location and years, column 2 shows the seedling vigor score (1 to 5 where 5 is best), column 3 shows the days to 50% heading, column 4 shows the mature plant height in centimeters (cm) and column 5 shows the percent (%) lodging.

TABLE 5

| Location | Seedling Vigor | Days to 50% Heading | Plant Height (cm) | Lodging (%) |
|---|---|---|---|---|
| Early SW 2010-2014 Mean | | | | |
| Butte | 5.0 | 88 | 97 | 4 |
| Colusa | 5.0 | 93 | 100 | 6 |
| Biggs | 4.8 | 88 | 96 | 1 |
| Yuba | 5.0 | 95 | 105 | 17 |
| Overall Mean | 4.9 | 91 | 100 | 7 |
| Very Early SW 2012-2014 Mean | | | | |
| Biggs | 4.8 | 87 | 99 | 0 |
| San Joaquin | 5.0 | 111 | 83 | 1 |
| Sutter | 5.0 | 91 | 95 | 18 |
| Yolo | 5.0 | 90 | 105 | 40 |
| Overall Mean | 4.9 | 95 | 95 | 15 |
| Intermediate-Late SW 2013-2014 Mean | | | | |
| Glenn | 4.8 | 94 | 104 | 1 |
| Biggs | 4.9 | 86 | 101 | 0 |
| Sutter-West | 5.0 | 90 | 104 | 50 |
| Overall Mean | 4.9 | 90 | 103 | 17 |
| Grand Mean | 4.9 | 92 | 99 | 11 |

Table 6 shows the grain dimensions and brown rice 1000 kernel weight of M-209 compared to rice cultivars M-205 and M-206. Samples were collected from the Rice Experiment Station (RES) in Biggs, Calif. in 2014. Column 1 shows the variety, columns 2-4, 5-7, and 8-10 show length in millimeters (mm), width (mm) and 1000 kernel weight in grams (g) for paddy, brown, and milled rice, respectively, and column 11 shows the length/width ratio for the milled rice. As shown in Table 6, M-209 has larger, heavier kernels than M-205 and M-206.

TABLE 6

| Variety | Paddy Rice | | | Brown Rice | | | Milled Rice | | | L/W Ratio |
|---|---|---|---|---|---|---|---|---|---|---|
| | Length (mm) | Width (mm) | 1000-wt. (g) | Length (mm) | Width (mm) | 1000-wt. (g) | Length (mm) | Width (mm) | 1000-wt. (g) | |
| M-209 | 8.47 | 3.20 | 29.7 | 6.23 | 2.78 | 24.6 | 5.94 | 2.70 | 22.1 | 2.20 |
| M-205 | 8.41 | 3.13 | 28.1 | 6.04 | 2.78 | 23.4 | 5.87 | 2.69 | 21.4 | 2.18 |
| M-206 | 8.16 | 3.19 | 28.1 | 5.90 | 2.79 | 23.3 | 5.70 | 2.72 | 21.3 | 2.10 |

Table 7 shows the average head (whole kernel) and total milled rice from harvest moisture milling studies conducted at the Rice Experiment Station from 2011-2014. Column 1 shows the entry and columns 2-4 show head and total milled rice, and the number of samples collected in that harvest moisture range in parentheses.

TABLE 7

| | % Head/Total Milled Rice (No. of Samples) Harvest Moisture Range | | |
|---|---|---|---|
| Entry | Above 22% | 18-22% | Below 18% |
| M-209 | 62/69 (9) | 65/71 (11) | 64/72 (5) |
| M-202 | 63/68 (10) | 62/67 (11) | 57/67 (8) |
| M-205 | 65/70 (10) | 65/70 (16) | 63/71 (10) |
| M-206 | 65/70 (12) | 66/70 (13) | 63/70 (7) |

Table 8 shows a summary of the results of laboratory analysis of several quality components of rice. Rapid Visco Analysis (RVA), apparent amylose, and protein percentage data for M-209 (08Y3269), M-202, M-205, and M-206 taken from 2012 to 2013 data through independent external evaluations (USDA-ARS and the California Wheat Commission) are shown. Column 1 shows the year, column 2 shows the variety, column 3 shows the peak, column 4 shows the trough, column 5 shows the breakdown, column 6 shows the final viscosity, column 7 shows the setback, column 8 shows the apparent amylose (%), column 9 shows the protein (%) and column 10 shows the gel type. Results show that M-209 follows the quality pattern of a California Calrose temperate *japonica* medium grain rice.

TABLE 8

| Year | Variety | Peak | Trough | Breakdown | Final Visc. | Setback | Apparent Amylose (%) | Protein (%) | Gel Type |
|---|---|---|---|---|---|---|---|---|---|
| 2012 | M-209 | 290.1 | 164.8 | 125.3 | 270.3 | −19.8 | 18.1 | 6.7 | Low |
| | M-202 | 346.5 | 176.8 | 169.8 | 280.2 | −66.3 | 16.3 | 5.4 | Low |
| | M-205 | 304.8 | 176.1 | 128.8 | 291.3 | −13.6 | 17.4 | 7.3 | Low |
| | M-206 | 309.1 | 178.6 | 130.5 | 286.5 | −22.6 | 18.0 | 7.0 | Low |
| 2013 | M-209 | 233.7 | 122.4 | 111.3 | 233.7 | 0.0 | 16.1 | 5.8 | Low |
| | M-202 | 264.4 | 125.1 | 139.3 | 221.2 | −43.2 | 14.7 | 6.2 | Low |
| | M-205 | 235.3 | 123.5 | 111.8 | 229.5 | −5.8 | 16.3 | 5.6 | Low |
| | M-206 | 235.7 | 116.5 | 119.2 | 227.5 | −8.2 | 16.6 | 6.5 | Low |
| Mean | M-209 | 261.9 | 143.6 | 118.3 | 252.0 | −9.9 | 17.1 | 6.3 | Low |
| | M-202 | 305.5 | 150.9 | 154.5 | 250.7 | −54.8 | 15.5 | 5.8 | Low |
| | M-205 | 270.1 | 149.8 | 120.3 | 260.4 | −9.7 | 16.9 | 6.4 | Low |
| | M-206 | 272.4 | 147.6 | 124.8 | 257.0 | −15.4 | 17.3 | 6.8 | Low |

Table 9 shows a summary of the results of cold-induced blanking in San Joaquin (SJ) and at RES using a refrigerated greenhouse (GH). Measuring blanking tolerance is difficult, whether the test is performed in the field or in the greenhouse. Seasonal temperature variation as well as variation in heading dates of test entries complicates field measurements. Similarly, GH test conditions are harsher compared to actual field conditions and keeping the temperature fluctuations to a minimum throughout the greenhouse is difficult. Column 1 shows the year, column 2 shows the test, where SJ indicates cold-induced blanking in San Joaquin and GH indicates cold-induced blanking using a refrigerated greenhouse at RES, and columns 3-6 show the blanking % on the various varieties. The value in parenthesis is the total number of data points used to calculate overall mean. In San Joaquin (SJ), M-209 blanking ranged from 2-6% in the period from 2012 to 2014, while the GH tests showed a wider spread of 13-20%. Overall, combined tests indicate that M-209 had an average blanking of 12.6% compared to 11.8%, 12.1%, and 10.6% for M-202, M-205, and M-206, respectively. These results indicate that M-209 may suffer more from cold-induced blanking if grown in cooler rice areas.

TABLE 9

| | | Blanking % | | | |
|---|---|---|---|---|---|
| Year | Test | M-209 | M-202 | M-205 | M-206 |
| 2012 | GH | 20 | 19 | 17 | 15 |
| | SJ | 6 | 5 | 5 | 5 |
| 2013 | GH | 16 | 16 | 15 | 14 |
| | SJ | 4 | 4 | 6 | 8 |
| 2014 | GH | 13 | 10 | 17 | 12 |
| | SJ | 2 | 2 | 2 | 1 |
| MEAN | | 12.6 (47) | 11.8 (94) | 12.1 (106) | 10.6 (108) |

Table 10 shows a summary of reactions to stem rot, aggregate sheath spot, and blast diseases for rice cultivar M-209 compared to rice cultivars M-202, M-205, M-206 and M-208. Column 1 shows the year, column 2 shows the variety name, column 3 shows the stem rot score, column 4 shows the aggregate sheath spot score and column 5 shows the blast score. In Table 10, for the stem rot score, 3 indicates that all but one leaf sheath was penetrated, 4 indicates that all were penetrated, 5 indicates that all were penetrated but not the culm, 6 indicates penetration of the culm surface layer, and 7 indicates that 25% of culm were girdled. For the aggregate sheath spot score, 0 indicates none of the four uppermost leaves were damaged, 2 indicates that the bottom one of four leaves were damaged, and 3 indicates that the bottom two of four leaves were damaged. For the blast score, 0 indicates no symptoms, 1 indicates pinhead, 2 indicates less than 25% leaf area with susceptible lesions, 3 indicates greater than 25%, but less than 75% leaf area with susceptible lesions, and 4 indicates that the plants were dead.

As shown in Table 10, the results indicate that M-209 had a comparable average reaction to stem rot compared to M-205 and a better reaction compared to M-202, M-206, and M-208. Rice cultivar M-209 had a better reaction to aggregate sheath spot compared to M-206 and M-208. However, M-209, having no blast resistance gene to the blast pathogen as M-202 and M-206, had greater susceptibility to the disease than M-208.

TABLE 10

| Year | Variety | Stem rot Score | Aggregate Sheath Spot Score | Blast Score |
|---|---|---|---|---|
| 2010 | M-209 | 4.9 | — | — |
| | M-202 | 5.6 | — | — |
| | M-205 | 5.3 | — | — |
| | M-206 | 5.3 | — | — |
| | M-208 | 5.5 | — | — |
| 2011 | M-209 | 5.2 | 2.8 | — |
| | M-202 | 5.4 | 2.4 | — |
| | M-205 | 4.7 | 2.5 | — |
| | M-206 | 5.4 | 2.8 | — |
| | M-208 | 5.6 | 2.8 | — |
| 2012 | M-209 | 4.5 | 1.7 | — |
| | M-202 | 4.5 | 1.6 | — |
| | M-205 | 4.2 | 1.5 | — |
| | M-206 | 4.5 | 2.8 | — |
| | M-208 | 5.1 | 2.8 | — |
| 2013 | M-209 | 5.2 | 1.4 | 3.5 |
| | M-202 | 6.1 | 1.7 | 3.3 |
| | M-205 | 5.3 | 1.8 | 3.0 |
| | M-206 | 7.0 | 2.3 | 3.3 |
| | M-208 | 6.3 | 2.2 | 0.5 |
| 2014 | M-209 | 4.7 | 1.8 | 2.2 |
| | M-202 | 4.9 | 1.8 | 2.2 |
| | M-205 | 4.5 | 1.8 | 2.3 |
| | M-206 | 4.7 | 2.0 | 1.5 |
| | M-208 | 5.3 | 2.3 | 2.7 |
| Mean | M-209 | 4.9 | 1.9 | 2.8 |
| | M-202 | 5.3 | 1.9 | 2.7 |
| | M-205 | 4.8 | 1.9 | 2.6 |
| | M-206 | 5.4 | 2.5 | 2.4 |
| | M-208 | 5.6 | 2.5 | 1.6 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the California Cooperative Rice Research Foundation, Inc. proprietary Rice Cultivar M-209 disclosed above and recited in the appended claims has been made with the American Type Culture Collection (ATCC), 10801 University Boulevard, Manassas, Va. 20110 under the terms of the Budapest Treaty. The date of deposit was Jan. 27, 2016. The deposit of 2,500 seeds was taken from the same deposit maintained by California Cooperative Rice Research Foundation, Inc. since prior to the filing date of this application. All restrictions will be irrevocably removed upon granting of a patent, and the deposit is intended to meet all of the requirements of 37 C.F.R. §§1.801-1.809. The ATCC Accession Number is PTA-122792. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of rice cultivar M-209, wherein a representative sample of seed of said cultivar has been deposited under ATCC Accession No. PTA-122792.

2. A rice plant, or a part thereof, produced by growing the seed of claim 1.

3. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flower, stem, glumes and panicle.

4. A protoplast produced from the plant of claim 2.

5. A protoplast produced from the tissue culture of claim 3.

6. A rice plant regenerated from the tissue culture of claim 3, wherein the plant has all of the morphological and physiological characteristics of rice cultivar M-209.

7. A method for producing an $F_1$ hybrid rice seed, wherein the method comprises crossing the plant of claim 2 with a different rice plant and harvesting the resultant $F_1$ hybrid rice seed.

8. A hybrid rice seed produced by the method of claim 7.

9. A hybrid rice plant, or a part thereof, produced by growing said hybrid rice seed of claim 8.

10. A method of producing an herbicide resistant rice plant, wherein the method comprises transforming the rice plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

11. An herbicide resistant rice plant produced by the method of claim 10.

12. A method of producing an insect resistant rice plant, wherein the method comprises transforming the rice plant of claim 2 with a transgene that confers insect resistance.

13. An insect resistant rice plant produced by the method of claim 12.

14. The rice plant of claim 13, wherein the transgene encodes a *Bacillus thuringiensis* endotoxin.

15. A method of producing a disease resistant rice plant, wherein the method comprises transforming the rice plant of claim 2 with a transgene that confers disease resistance.

16. A disease resistant rice plant produced by the method of claim 15.

17. A method of producing a rice plant with modified fatty acid metabolism or modified carbohydrate metabolism, wherein the method comprises transforming the rice plant of claim 2 with a transgene encoding a protein selected from the group consisting of fructosyltransferase, levansucrase, alpha-amylase, invertase and starch branching enzyme or DNA encoding an antisense of stearyl-ACP desaturase.

18. A rice plant having modified fatty acid metabolism or modified carbohydrate metabolism produced by the method of claim 17.

19. A method of introducing a desired trait into rice cultivar M-209, wherein the method comprises:
(a) crossing a M-209 plant, wherein a representative sample of seed was deposited under ATCC Accession No. PTA-122792, with a plant of another rice cultivar that comprises a desired trait to produce progeny plants, wherein the desired trait is selected from the group consisting of male sterility, herbicide resistance, insect resistance, abiotic stress tolerance, modified fatty acid metabolism, modified carbohydrate metabolism and resistance to bacterial disease, fungal disease or viral disease;
(b) selecting one or more progeny plants that have the desired trait;
(c) backcrossing the selected progeny plants with the M-209 plants to produce backcross progeny plants;
(d) selecting for backcross progeny plants that have the desired trait; and
(e) repeating steps (c) and (d) three or more times to produce selected fourth or higher backcross progeny plants that comprise the desired trait.

20. A plant produced by the method of claim 19, wherein the plant has the desired trait and otherwise all of the physiological and morphological characteristics of rice cultivar M-209.

21. The plant of claim 20, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

22. The plant of claim 20, wherein the desired trait is insect resistance and the insect resistance is conferred by a transgene encoding a *Bacillus thuringiensis* endotoxin.

23. The plant of claim 20, wherein the desired trait is modified fatty acid metabolism or modified carbohydrate metabolism and said desired trait is conferred by a nucleic acid encoding a protein selected from the group consisting of fructosyltransferase, levansucrase, alpha-amylase, invertase and starch branching enzyme or DNA encoding an antisense of stearyl-ACP desaturase.

24. The plant of claim 20, wherein the desired trait is abiotic stress tolerance and said desired trait modifies tolerance to drought, flooding, salinity, or temperature change.

25. A method of introducing the head rice stability trait of rice cultivar M-209 into another rice cultivar, wherein the method comprises crossing a M-209 plant, wherein a representative sample of seed is deposited under ATCC Accession No. PTA-122792, with a plant of another rice cultivar and selecting for progeny plants that have head rice stability.

26. A rice plant produced by the method of claim 25, wherein said plant has the desired trait and otherwise all of the physiological and morphological characteristics of rice cultivar M-209.

27. A method of producing a rice plant with a desired trait, wherein the method comprises introducing a gene mutation via chemical mutagenesis into the rice plant of claim 2.

28. A rice plant produced by the method of claim 27, wherein said plant has the desired trait and otherwise all of the physiological and morphological traits of rice cultivar M-209.

29. A method of producing a commodity plant product, comprising obtaining the plant of claim 2, or a part thereof, and producing the commodity plant product from said plant or plant part thereof, wherein said commodity plant product is selected from the group consisting of meal, flour, oil, film, packaging, and nutraceutical product.

* * * * *